United States Patent [19]

Blackborow et al.

[11] Patent Number: 5,103,061
[45] Date of Patent: Apr. 7, 1992

[54] SYNTHESIS OF HYDROCARBYL AMINES

[75] Inventors: John R. Blackborow, Aix en Provence; Regis Peretti, Marseille, both of France

[73] Assignee: BP Chemicals Limited, London, United Kingdom

[21] Appl. No.: 571,652

[22] PCT Filed: Feb. 10, 1989

[86] PCT No.: PCT/GB90/00144

§ 371 Date: Sep. 6, 1990

§ 102(e) Date: Sep. 6, 1990

[87] PCT Pub. No.: WO90/09371

PCT Pub. Date: Aug. 23, 1990

[30] Foreign Application Priority Data

Feb. 10, 1989 [EP] European Pat. Off. ......... 89400383

[51] Int. Cl.$^5$ ............................................. C07C 209/26
[52] U.S. Cl. ...................... 564/472; 525/333.8; 525/379
[58] Field of Search ............. 564/472; 525/333.8, 525/379

[56] References Cited

U.S. PATENT DOCUMENTS

| | | | |
|---|---|---|---|
| 3,076,791 | 2/1963 | Hollyday et al. | 525/329.6 |
| 3,293,112 | 12/1966 | Kohr | 525/379 |
| 3,350,381 | 10/1967 | Moeller | 525/333.8 |
| 3,647,691 | 3/1972 | Vineyard | 564/157 |
| 3,756,954 | 9/1973 | Abbott et al. | 525/333.8 |
| 3,756,999 | 9/1973 | Stetter et al. | 525/333.8 |
| 3,769,216 | 10/1973 | Gordon et al. | 525/333.8 |
| 3,785,980 | 1/1974 | Wilgus | 525/333.8 |
| 3,980,682 | 9/1976 | Danner et al. | 525/333.8 |
| 4,113,636 | 9/1978 | Engel et al. | 252/51.5 |
| 4,832,702 | 5/1989 | Kummer et al. | 525/379 |
| 5,028,666 | 7/1991 | Clarke | 525/333.8 |

FOREIGN PATENT DOCUMENTS

| | | | |
|---|---|---|---|
| 244616 | 11/1987 | European Pat. Off. | |
| 384314 | 11/1932 | United Kingdom | 564/472 |
| 1027410 | 4/1966 | United Kingdom | |
| 1172818 | 12/1969 | United Kingdom | |

Primary Examiner—Richard L. Raymond
Assistant Examiner—Scott C. Rand
Attorney, Agent, or Firm—Brooks Haidt Haffner & Delahunty

[57] ABSTRACT

This invention relates to a process for producing long chain alkyl amines from polyolefins by reacting (a) a polyolefin having a molecular weight in the range of 330-2000 with ozone in the presence of a solvent, (b) reacting the ozonolysis product from (a) without separation and/or isolation of the carbonyl compounds formed therein with primary hydrocarbyl amines to form an imine, (c) hydrogenating the imine from step (b) to an amine in the presence of a hydrogenation catalyst, and (d) recovering the long chain alkyl amine from the hydrogenation products formed in step (c). The amines so produced are useful gasoline and lube oil additives.

10 Claims, No Drawings

SYNTHESIS OF HYDROCARBYL AMINES

This invention relates to a process for producing hydrocarbyl amines suitable for use as lube oil or gasoline additives.

Methods of producing nitrogen derivatives having long chain hydrocarbyl chains are well known. For instance GB-A-1172818 (Monsanto) describes a process for producing Schiff's bases by oxidising a polyolefin with ozone in the presence of an alcohol followed by conversion of the oxidation product to a carbonyl compound and reaction of the carbonyl compound after separation thereof from the ozonolysis products with an amine results in a Schiffs base.

This necessary separation and/or purification of the carbonyl compound from the ozonolysis products prior to reaction with an amine would appear to make the process commercially non-viable.

An alternative method is that described in EP-A-244616 (BASF AG) where a polybutene is subjected to a hydroformylation reaction and the resultant mixture of oxo products is subjected to either (a) a Mannich reaction or (b) a hydroamination reaction.

This reaction has the disadvantage that the hydroformylation product has a mixture of long chain aldehydes, ketones and long chain alcohols. Such a mixture of products, especially the presence of long chain alcohols, which are not separated prior to the Mannich reaction or hydroamination, give a complicated mixture of products.

Moreover, the long chain alcohols may have a detrimental effect on the aminated end product when used eg. as lube oil additives or gasoline additives.

It has now been found that the problems associated with such prior art process can be mitigated by (a) avoiding the separation steps of the GB-A-1172818 and also the hydroformylation step of E-A-244616.

Accordingly, the present invention is a process for producing long chain alkyl amines from polyolefins, said process comprising reacting (a) a polyolefin having a molecular weight in the range of 330-2000 with ozone in the presence of a solvent, (b) reacting the ozonolysis product from (a) without separation and/or isolation of the carbonyl compounds formed therein with a primary hydrocarbyl amines to form an imine, (c) hydrogenating the imine from step (b) to an amine in the presence of a hydrogenation catalyst, and (d) recovering the long chain alkyl amine from the hydrogenation products formed in step (c).

The polyolefin which is ozonolysed is suitably a polymer of a $C_2$-$C_4$ olefin or a copolymer thereof and has a molecular weight in the region of 330–2000, preferably from 500 to 1500. Of these, polybutenes, especially those containing significant proportions of polyisobutene i.e. Hyvis, Napvis and Ultravis (all Registered Trade Marks, ex BP Chemicals) are preferred.

The ozonolysis of the polyolefin in step (a) above is suitably carried out by bubbling ozone in the gaseous phase, with or without an additional diluent, through a solution of the polyolefin in a solvent. Examples of solvents that may be used include alcohols and hydrocarbons, preferably aliphatic, straight chain alcohols which have 1-12 carbon atoms in the chain. In the case of alcohols, these preferably have 1-4 carbon atoms in the chain.

The ozonolysis temperature is suitably from $-70°$ to $+50°$ C., preferably $-30°$ to $+30°$ C., and most preferably from $-10°$ to $+30°$ C. The reaction is exothermic and hence care should be taken to ensure that the reaction temperature does not exceed 50° C., if necessary by cooling.

The solvent is suitably present in the reaction mixture in a weight ratio of 1:1 to 10:1 with respect to the polyolefin reactant.

For this reaction it is essential to ensure that the proportion of ozone to olefin reacted at a given temperature and pressure are such that no explosive mixtures are formed. The explosive limits for the various reaction conditions are well known to those skilled in the art.

The ozonolysis products from step (a) are contacted with a primary amine in step (b). For this step the ozonolysis products are used directly, i.e. without any prior separation step, for reaction with the primary amine. Prior to contact of the ozonolysis products with the primary amine, it is preferable to (i) remove any excess ozone therein by sparging an inert gas eg. nitrogen therethrough and (ii) to wash the ozonolysis products with water in order to remove any lower boiling fractions such as eg. acetone.

The primary hydrocarbyl amines used to react with the ozonolysis product may be one or move of mono- di- and polyamines which may be aliphatic, alicyclic or aromatic in nature.

Typical examples of amines which can be used in preparing compounds of this invention are diethylenetriamine, di(methylethylene)triamine, triethylenetetramine, tri(methylethylene)tetramine, tri(ethylethylene)tetramine, tetraethylenepentamine, pentaethylenehexamine, ethylenediamine, hexamethylenediamine, o-phenylenediamine, m- phenylenediamine, p -phenylenediamine, alkyl-substituted o-, m- and p - phenylenediamine, dimethylaminomethylamine, dimethylaminoethylamine, dimethylaminopropylamine, dimethylaminobutylamine, dimethylaminoheptylamine, diethylaminomethylamine, diethylaminopropylamine, diethylaminoamylamine, dipropylaminopropylamine, methylpropylaminoamylamine, propylbutylaminoethylamine, dimethylenetrianilinemethylenedianiline, polymethyleneaniline and polyalkylmethyleneaniline.

The reaction of the ozonolysis product from step (a) with the primary amine in step (b) is suitably carried out at a temperature in the range of e.g. 50°-200° C. This reaction with primary amine is carried out by continuous removal of water formed during the reaction along with any incidental volatilization of solvents already present in the reaction mixture.

In this reaction the molar ratio of the ozonolysis products to the primary amine is suitably from 1:1 to 1000:1, preferably from 1:1 to 5:1.

The product of the reaction in step (b) is a hydrocarbyl imine. Also present in this product are water and solvents specially those used for step (a) above.

The water and solvents are separated from the imine product by eg. filtration and/or fractional distillation.

The separated imine product from step (b) is then hydrogenated to form the desired amine.

The hydrogeneration of the imine may be carried out under homogeneous or heterogeneous conditions.

The hydrogenation is carried out using catalyst such as Raney nickel, cobalt, ruthenium, rhodium, iridium, platinum especially platinum on carbon, palladium on carbon, palladium on silica and the like.

The hydrogenation reaction is suitably carried out a pressure of up to 20 MPa, preferably from up to 10 MPa. more preferably from up to 8 MPa.

The hydrogenation reaction is suitably carried out at a temperature from 0° to 200° C., preferably from 50° to 150° C.

Where the hydrogenation reaction is carried out under heterogeneous conditions, the removal of catalyst residues is facilitated. For this purpose, solvent extraction of the amine product can be used. The preferred solvents are aliphatic alcohols or hydrocarbons.

It is, in fact, possible to carry out the imination of the ozonolysis products and the hydrogenation of the imine so formed to the corresponding amine in a single reactor thus avoiding the need to separate/purify the products of step (b). Thus, the recommended conditions for the imination step (b) above and the hydrogenation step (c) above can be used sequentially in a single reactor without recovering the intermediate imine. Typically, this may be achieved by initially allowing the imination reaction to proceed until upto 60% w/w of the ozonolysis product has been converted to the imine and then hydrogenating in the same reactor the crude imination product so formed, without any separation steps.

Alternatively, by a suitable choice of hydrogenation catalyst both the imination of the carbonyl compound and the hydrogenation of the imine can be performed substantially simultaneously such that any imine formed is instantaneously hydrogenated to the amine. Thus there is no need to wait for any significant quantities of the imine to be formed prior to commencement of the hydrogenation step.

The desired amine can thus be recovered from the reaction products of hydrogenation by filtering off the catalyst and removing the solvent from the filtrate by distillation.

The hydrocarbyl amines of the present invention can be used as lube oil additives, fuel additives and as gasoline detergents.

The present invention is further illustrated with reference to the following Examples.

EXAMPLE 1

Production Imines

A(a) In a tubular glass vessel equipped with a gas disperser at its base and an isothermal jacket was placed 100 g of a polyisobutene (NAPVIS 10, RTM) of Mn = 1000 and 100 ml of n-hexane. Ozone was then passed through the polyisobutene solvent mixture at 15° C. at the rate of 0.13 moles per hour. After four hours the ozone supply was stopped and nitrogen was passed through the reaction mixture or a short time (2 minutes) to remove any unreacted ozone in the vessel which now contained the ozonlysis products.

(b) 0.2 moles of dimethylaminopropylamine was then added to the ozonolysis products whilst the passage of nitrogen was continued for a further 2 minutes. The contents of the vessel were then transferred to a glass reactor (500 ml capacity) equipped with a condenser. The contents of the reactor were refluxed (71° C.) for 2 hours and finally the reaction mixture evaporated in a rotary evaporator under vacuum at 140° C. using an oil bath. The non-volatile residue remaining after evaporation was the imine intermediate which was yellow and contained 1.8%w/w nitrogen 115 g of product was recovered with an imine yield of approximately 64% molar.

B(a) In a tubular glass reactor, which was about five times larger in diameter than the used in A(a) above, was placed 650 g of a polyisobutene of Mn 1000 and a mixture of n-hexane and methanol (300 ml) each). Ozone containing small quantities of air was passed through the polyisobutene/solvent mixture with vigorous stirring. During this operation further aliquots of a 50/50 wt % mixture of n-hexane and methanol (total 300 ml) was added from time to time. The reaction proceeded for 6.5 hours. The ozone supply was thereafter stopped and the reaction mixture sparged with nitrogen to remove any unreacted ozone therein. Thereafter water (300 ml) was added to the reaction mixture. The whole contents of the reactor were then transferred to another vessel and the aqueous phase allowed to separate. This happened readily and the aqueous layer was removed.

(b) 220 g of the non-purified organic product was mixed with 800 ml of toluene and 24.74 g of commercial tetraethylene pentamine in 200 ml of toluene. The whole mixture was heated to boiling and 400 ml of solvent removed after 4 hours. The remaining solvent was removed in a rotary evaporator under oil pump vacuum at 140° C.

240 g of product was recovered from the evaporator and contained 3.1% w/w nitrogen corresponding to an imine yield of approximately 66% molar.

A comparison of the above A and B processes shows that much less ozone is needed in a stirred reactor than in an non-stirred reactor for similar imine yields.

Hydrogenation of Imine 70 g of the imine product form procedure of Example 1(A) above was placed in a high pressure autoclave (300 ml) capacity equipped with a mechanical stirrer together with a 80 ml of cyclohexane. 5 g of a freshly ethanol-washed commercial sample of Raney nickel together with 20 ml ethanol was also added to the autoclave which was then sealed and degassed with hydrogen. The contents of the autoclave were vigorously stirred under a hydrogen atmosphere for 15 Mpa (150 bars) and maintained at 90° C. for 19 hours. The stirring was stopped and the contents of the autoclave allowed to cool and subsequently depressurised. The reaction mixture was filtered and the filtrate evaporated on a rotary evaporator as in Example 1(A) above. The resultant straw coloured residue showed negligible adsorption in the infra-red spectral region of 1800 cm$^{-1}$ and 1600 cm$^{-1}$ signifying the absence any imine or carbonyl functions in the product. The product had a nitrogen content of 1% w/w.

EXAMPLE 2

Imination and Hydrogenation in a single step:

401 g of a polybutene (Mn = 1300) was mixed by stirring with 400 ml of n-octane and 25 ml of methanol; 0.13 moles/hr of ozone in air were passed through the stirred mixture for 3.5 hr after which 500 ml of water were mixed with the reactants and the mixture was allowed to separate into aqueous and organic phases. The aqueous layer was run off and the organic layer mixed with 48 g of dimethylamino-propylamine in a hydrogenation reactor equipped with a Dean & Stark side arm. The contents of the reactor were refluxed for 3 hr and water removed via the Dean & Stark arm. Thereafter, 3.5 g of platinum on carbon (Pt 5% w/w) was added to the reactor and the reactor with its contents was pressurized to 2.8 MPa (28 bar) with hydrogen at 160° C. The hydrogenation reaction was continued over 20 hr with vigorous stirring.

The contents of the reactor were then discharged and filtered. The filtrate was treated by a rotary evaporation technique until all light fractions were removed to leave behind a viscous residue.

The viscous residue (560 cst at 100° C.) contained 1.2% w/w nitrogen and only traces of carbonyl or imine bands were detected in the infra-red spectrum of the product (<10 mole %).

EXAMPLE 3

Imination and Hydrogenation in a single step:

A mixture of 365 g of the imine of polybutene carbonyl of Mn=1300 and the polybutene carbonyl prepared according to the process of Example 2 above were mixed with 450 ml of n-octane and 3 g of 5% w/w platinum on carbon in a hydrogenation reactor. After 6hrs of hydrogenation at 130° C. at a pressure between 2.0–3.0 MPa (20–30 bars) a sample was taken and subjected to rotary evaporation at 165° C. for 1hr at 4 mm of Hg pressure to remove light fractions leaving behind a viscous residue. The infra-red spectrum of the residue showed a small imine band and a carbonyl band.

The hydrogenation of the bulk product was continued for a further 6 hr and the sampling procedure repeated. The infra-red spectrum of the sample residue (after rotary evaporation as previously) now showed a trace of an imine band and a persistent carbonyl band.

The hydrogenation of the bulk was continued for a further 6 hr but now in the presence of 27 ml of dimethylamino-propylamine and again the sampling procedure was repeated as previously. This time it was noted that the carbonyl band had disappeared almost completely from the infr-red spectrum of the sample residue.

The bulk contents of the reactor were then filtered and treated by a rotary evaporation technique to remove all light and unreacted materials and a viscous residue was left behind. The residue was pale yellow and contained approximately 1.5% w/w of basic nitrogen.

The NMR spectrum of the residue showed the presence of a polybutene polyamine.

This Example shows that a platinum on carbon catalyst hydrogenates polybutene imines more readily than polybutene carbonyls and that in the presence of free amine, polybutene polyamines can be produced by a one-step hydroamination of a polybutene carbonyl

We claim:

1. A process for producing long chain alkyl amines from polyolefins, said process comprising reacting
   (a) a polyolefin having a molecular weight in the range of 330-2000 with ozone in the presence of a solvent,
   (b) reacting the ozonolysis product from (a) without separation and/or isolation of the carbonyl compounds formed therein with a primary hydrocarbyl amines to form an imine,
   (c) hydrogenating the imine from step (b) to an amine in the presence of a hydrogenation catalyst, and
   (d) recovering the long chain alkyl amine from the hydrogenation products formed in step (c).

2. A process according to claim 1 wherein the polyolefin which is ozonolysed is a polymer of a $C_2$–$C_4$ olefin or a copolymer thereof and has a molecular weight in the region of 330–2000.

3. A process according to claim 1 wherein the ozonolysis of the polyolefin in step (a) above is carried out by bubbling ozone in the gaseous phase, with or without an additional diluent, through a solution of the polyolefin in a solvent.

4. A process according to claim 1 wherein the ozonolysis temperature is from −70° to +50° C.

5. A process according to claim 1 wherein the primary hydrocarbyl amines used to react with the ozonolysis product is selected from one or more of mono- di- and polyamines which may be aliphatic, alicyclic or aromatic in nature.

6. A process according to claim 1 wherein the reaction of the ozonolysis product from step (a) with the primary amine in step (b) is carried out at a temperature from 50°–200° C.

7. A process according to claim 1 wherein in the reaction of the ozonolysis products with the primary amine, the respective molar ratios of the two is form 1:1 to 1000:1.

8. A process according to claim 1 wherein the hydrogenation of the imine from step (c) is carried out using catalyst such as Raney nickel, palladium on carbon or palladium on silica.

9. A process according to claim 1 wherein the hyrogenation reaction is carried out a pressure of up to 20 MPa.

10. A process according to claim 1 wherein the hydrogenation reaction is carried out at a temperature from 0° to 200° C.

* * * * *

UNITED STATES PATENT AND TRADEMARK OFFICE
CERTIFICATE OF CORRECTION

PATENT NO. : 5,103,061
DATED : April 7, 1992
INVENTOR(S) : JOHN R. BLACKBOROW et al It is certified that error appears in the above-identified patent and that said Letters Patent is hereby corrected as shown below:

Col. 2, l. 26, correct the spelling of the word "mo_re_"

Col. 4, l. 4, should read "(300 ml each)"

Col. 4, l. 33, correct the spelling of the word "f_rom_"

Signed and Sealed this

Fifteenth Day of June, 1993

Attest:

MICHAEL K. KIRK

Attesting Officer

Acting Commissioner of Patents and Trademarks